(12) United States Patent
Mundis et al.

(10) Patent No.: US 11,672,567 B2
(45) Date of Patent: Jun. 13, 2023

(54) SPINAL FIXATION CONSTRUCT AND METHODS OF USE

(71) Applicant: K2M, Inc., Leesburg, VA (US)

(72) Inventors: Gregory Mundis, San Diego, CA (US); Han Jo Kim, Ny, NY (US); John Ferguson, Auckland (NZ); Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 119 days.

(21) Appl. No.: 16/794,546

(22) Filed: Feb. 19, 2020

(65) Prior Publication Data
US 2020/0179013 A1     Jun. 11, 2020

Related U.S. Application Data

(60) Continuation of application No. 16/108,126, filed on Aug. 22, 2018, now Pat. No. 10,582,953, which is a
(Continued)

(51) Int. Cl.
*A61B 17/70*     (2006.01)
*A61B 17/86*     (2006.01)

(52) U.S. Cl.
CPC ........ *A61B 17/7031* (2013.01); *A61B 17/701* (2013.01); *A61B 17/7001* (2013.01);
(Continued)

(58) Field of Classification Search
CPC ............ A61B 17/7019; A61B 17/7022; A61B 17/7026; A61B 17/7029; A61B 17/7031; A61B 17/7053; A61B 17/7008
See application file for complete search history.

(56) References Cited

U.S. PATENT DOCUMENTS 5,312,410 A    5/1994   Miller et al.
5,449,361 A    9/1995   Preissman
(Continued)

FOREIGN PATENT DOCUMENTS

EP    0582857 A1    2/1994
EP    0649636 A2    4/1995
(Continued)

OTHER PUBLICATIONS

Australian Examination Report for Application No. 2016200919 dated Sep. 6, 2019, pp. 1-5.
European Search Report for EP16173488 dated Oct. 6, 2016.

*Primary Examiner* — Julianna N Harvey
(74) *Attorney, Agent, or Firm* — Lerner David LLP

(57) ABSTRACT

A spinal fixation construct for aligning vertebral bodies includes a bone screw, a spinal rod, a flexible member, and a fixation member. The spinal rod is disposed within a saddle portion of a housing of the bone screw, and includes an elongated body having a first end and a second end. The spinal rod is formed from a first material having a first modulus of elasticity. The flexible member is coupled to the spinal rod, and includes an elongated body having a first end portion and a second end portion. The flexible member is formed from a second material having a second modulus of elasticity that is different from the first modulus of elasticity. The fixation member includes a threaded body portion and a head portion defining a hole therethrough. A portion of the flexible member extends through the hole of the head portion.

20 Claims, 11 Drawing Sheets

Related U.S. Application Data division of application No. 15/042,184, filed on Feb. 12, 2016, now Pat. No. 10,064,656.

(60) Provisional application No. 62/115,259, filed on Feb. 12, 2015.

(52) U.S. Cl.
CPC ...... *A61B 17/7004* (2013.01); *A61B 17/7022* (2013.01); *A61B 17/7037* (2013.01); *A61B 17/7053* (2013.01); *A61B 17/7067* (2013.01); *A61B 17/8605* (2013.01); *A61B 17/863* (2013.01)

(56) References Cited

U.S. PATENT DOCUMENTS

| | | | |
|---|---|---|---|
| 5,496,318 | A | 3/1996 | Howland et al. |
| 6,086,590 | A | 7/2000 | Margulies et al. |
| 6,582,434 | B2 * | 6/2003 | Kawakami ......... A61B 17/7002 606/276 |
| 8,162,946 | B2 | 4/2012 | Baccelli et al. |
| 8,465,495 | B2 | 6/2013 | Belliard |
| 8,486,110 | B2 | 7/2013 | Fielding et al. |
| 8,882,817 | B2 | 11/2014 | Jones et al. |
| 9,433,441 | B2 | 9/2016 | George et al. |
| 9,757,167 | B2 | 9/2017 | Hsu et al. |
| 10,034,692 | B2 | 7/2018 | Palmer et al. |
| 10,548,644 | B2 | 2/2020 | George et al. |
| 10,575,879 | B2 | 3/2020 | Palmer et al. |
| 2002/0116013 | A1 | 8/2002 | Gleason et al. |
| 2005/0101956 | A1 | 5/2005 | Simonson |
| 2005/0277929 | A1 * | 12/2005 | Raiszadeh ......... A61B 17/7053 606/279 |
| 2006/0217713 | A1 | 9/2006 | Serhan et al. |
| 2006/0229607 | A1 | 10/2006 | Brumfield |
| 2007/0088359 | A1 * | 4/2007 | Woods ............... A61B 17/7049 606/86 A |
| 2008/0262546 | A1 | 10/2008 | Calvosa et al. |
| 2008/0269805 | A1 | 10/2008 | Dekutoski et al. |
| 2009/0204118 | A1 | 8/2009 | Pratt |
| 2010/0160968 | A1 * | 6/2010 | Joshi ................. A61B 17/7026 606/257 |
| 2010/0185243 | A1 | 7/2010 | Pasquet et al. |
| 2011/0009906 | A1 * | 1/2011 | Hestad ............... A61B 17/7022 606/278 |
| 2011/0066187 | A1 * | 3/2011 | Fang ................. A61B 17/7052 606/254 |
| 2011/0106185 | A1 | 5/2011 | Gil et al. |
| 2011/0238118 | A1 | 9/2011 | Baccelli et al. |
| 2011/0301644 | A1 | 12/2011 | Belliard |
| 2012/0271356 | A1 | 10/2012 | Ramsay et al. |
| 2013/0013003 | A1 | 1/2013 | Carbone et al. |
| 2013/0041410 | A1 | 2/2013 | Hestad et al. |
| 2013/0072983 | A1 | 3/2013 | Lindquist et al. |
| 2013/0144342 | A1 | 6/2013 | Strauss et al. |
| 2013/0253587 | A1 * | 9/2013 | Carls ................. A61B 17/7022 606/279 |
| 2014/0025116 | A1 | 1/2014 | Wei |
| 2014/0094850 | A1 | 4/2014 | Clement et al. |
| 2014/0094851 | A1 * | 4/2014 | Gordon ............. A61B 17/809 606/264 |
| 2014/0257397 | A1 | 9/2014 | Akbarnia et al. |
| 2014/0277142 | A1 | 9/2014 | Blain et al. |
| 2016/0324549 | A1 * | 11/2016 | Blain ................. A61B 17/7035 |

FOREIGN PATENT DOCUMENTS

| | | |
|---|---|---|
| EP | 2052689 A1 | 4/2009 |
| EP | 2138122 A1 | 12/2009 |
| EP | 2316363 A1 | 5/2011 |
| WO | 2012176096 A1 | 12/2012 |
| WO | 2013001180 A1 | 1/2013 |

* cited by examiner

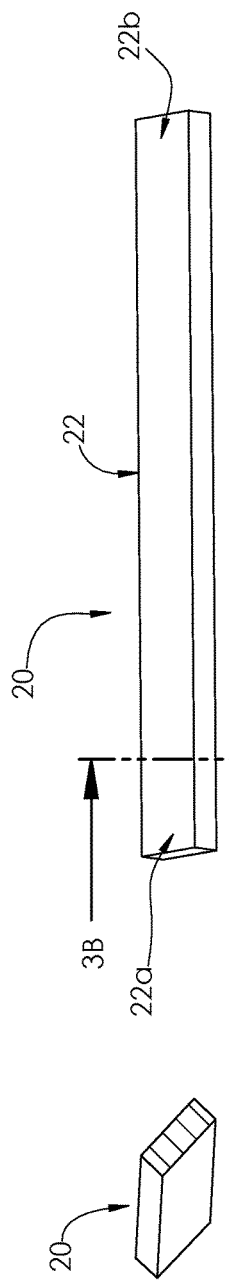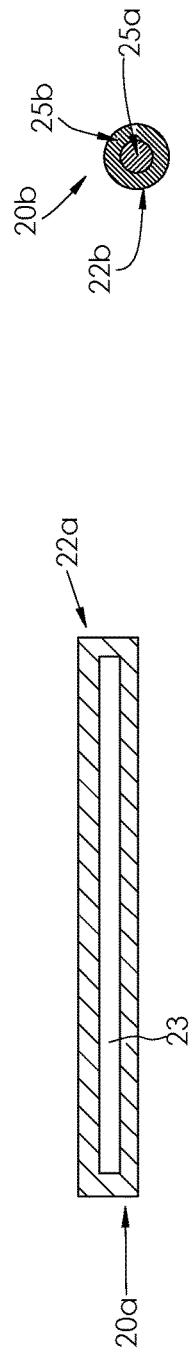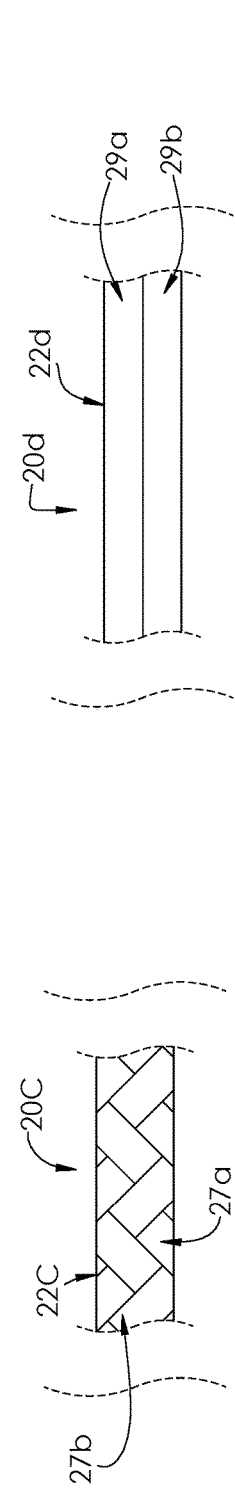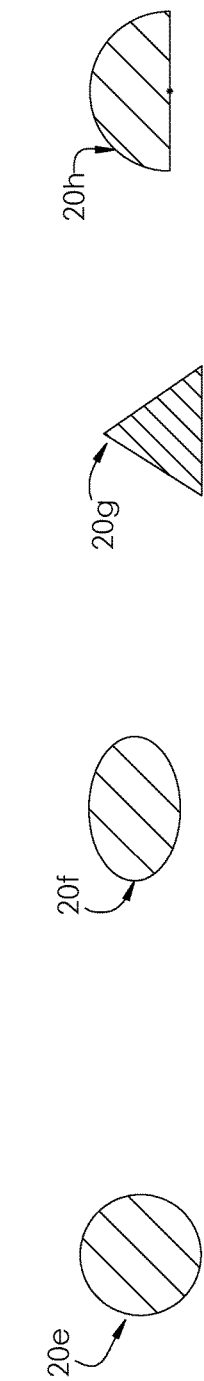

SPINAL FIXATION CONSTRUCT AND METHODS OF USE

CROSS-REFERENCE TO RELATED APPLICATIONS

The present application is a continuation of U.S/ patent application Ser. No. 16/108,126, filed on Aug. 22, 2018, which is a divisional application of U.S. patent application Ser. No. 15/042,184, now U.S. Pat. No. 10/064.656, filed on Feb. 12, 2016, which claims the benefit of, and priority to, U.S. Provisional Patent Application Ser. No. 62/115,259, filed on Feb. 12, 2015, the entire contents of each of which are incorporated herein by reference.

TECHNICAL FIELD

The present disclosure relates generally to spinal fixation devices, and more particularly, to a spinal fixation construct and methods of use in a spinal procedure.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal fixation devices are widely employed in surgical processes for correcting spinal injuries and diseases. When the disc has degenerated to the point of requiring removal, there are a variety of interbody implants that may be utilized to take the place of the disc. These include interbody spacers, metal cages, and cadaver and human bone implants. In order to facilitate stabilizing the spine and keeping the interbody in position, other implants are commonly employed, such as bone screws and spinal rods. Depending on the pathology and treatment, a surgeon will select the appropriate spinal rod material and size, specifically, the cross-sectional diameter of the spinal rod.

Subsequent to surgical treatment of a patient's spine is the occurrence of proximal junctional kyphosis (PJK). PJK is a spinal deformity condition that may occur if the lumbar lordosis and thoracic kyphosis are not properly restored post-surgery. PJK may also be caused by the accelerated degeneration of the joint capsules and smaller articular processes at one or two levels above or below the junctional region. PJK appears at or above the cranial-most thoracic level treated. Even though PJK most commonly occurs in the thoracic region of the spine, it can also occur in various spinal regions and may occur above or below the instrument levels and may impact the next adjacent level or two that is not instrumented. This type of failure is called adjacent level failure. Symptoms of PJK and adjacent level failure include pain, neurological deficit, ambulatory difficulty, and poor maintenance of sagittal balance. For patients that demonstrate these symptoms, often the only treatment is an additional surgery. The incidence rate of PJK may be upward of 50% of long construct, instrumented fusion cases. Factors contributing to this condition are the end vertebrae selection, facet violation, weakened structural support due to significant soft tissue disruption, extensive junctional paraspinal musculature dissection, and loss of integrity of the posterior tension band.

One thought to address the incidence of PJK is to decrease the structural rigidity of the construct at the top of the construct just below the proximal junction, thereby providing a transition from the relatively stiff instrumented spine to the more flexible, non-instrumented spine to minimize facet capsule and muscle disruption.

Spinal rods are typically made of cobalt chrome, stainless steel, or titanium alloy. However, in order to transition to a less stiff construct at the top, other less rigid materials may be employed to provide the desired stiffness.

A continuing need exists for an improved device, an improved system, and an improved method for performing spine surgery that does not create additional morbidity post-surgical treatment.

SUMMARY

The present disclosure is directed to fixing spinal vertebrae with a spinal fixation construct having varying stiffness properties along its length. A flexible member of the spinal fixation construct has reduced stiffness properties as compared to other components of the spinal fixation construct (e.g., a fixation member and/or a spinal rod).

In accordance with an aspect of the present disclosure, a spinal fixation construct for aligning vertebral bodies includes a bone screw, a spinal rod, a flexible member, and a fixation member. The bone screw includes a housing having a saddle portion and a bone screw member extending from the housing. The spinal rod is disposed within the saddle portion of the housing of the bone screw, and includes an elongated body having a first end and a second end. The spinal rod is formed from a first material having a first modulus of elasticity. The flexible member is coupled to the spinal rod, and includes an elongated body having a first end portion and a second end portion. The flexible member is formed from a second material having a second modulus of elasticity that is different from the first modulus of elasticity. The fixation member includes a threaded body portion and a head portion defining a hole therethrough. A first portion of the flexible member extends through the hole of the head portion of the fixation member.

The fixation member may be formed from a third material having a third modulus of elasticity that is different from the first modulus of elasticity. The first modulus of elasticity and/or the third modulus of elasticity may be higher than the second modulus of elasticity.

The hole of the fixation member may have a lateral dimension that is different from a longitudinal dimension of the hole.

In embodiments, the elongated body of the flexible member may be braided.

In some embodiments, the bone screw may include a set screw having external threads configured to engage internal threads of the housing, and the first and second end portions of the flexible member may be compressed against the spinal rod within the saddle portion of the housing and secured therein by the set screw.

The first end of the spinal rod may define an aperture therethrough, and a second portion of the flexible member may extend through the aperture. The second end of the spinal rod may also define an aperture therethrough.

In accordance with another aspect of the present disclosure, a method for aligning vertebral bodies includes implanting a bone screw into a vertebral body of a spine, positioning a portion of a spinal rod within a housing of the bone screw, the spinal rod formed from a first material having a first modulus of elasticity and including an elongated body having first and second ends, and securing a portion of a flexible member to the spinal rod, the flexible member formed from a second material having a second modulus of elasticity that is lower than the first modulus of elasticity, and including an elongated body having first and second end portions.

In embodiments, the method may further include passing a portion of the flexible member around a bony element of the spine. Passing the portion of the flexible member around the bony element may include at least one of looping the flexible member over a lamina, through a spinous process, or over a spinous process.

In some embodiments, securing the portion of the flexible member to the spinal rod includes placing the first and second end portions of the flexible member adjacent to the portion of the spinal rod positioned within the housing of the bone screw, and compressing the first and second end portions of the flexible member against the spinal rod with a set screw of the bone screw.

In embodiments, positioning the portion of the spinal rod may include the spinal rod having an aperture extending through at least one of the first or second ends, and securing the portion of the flexible member to the spinal rod may include passing the portion of the flexible member through the aperture of the spinal rod.

The method may further include tying the first and second end portions of the flexible member such that the flexible member forms a continuous loop.

In embodiments, the method may include implanting a fixation member into a bony element of the spine in spaced relation relative to the spinal rod, and securing a portion of the flexible member to the fixation member. The fixation member may include a head portion defining a hole therethrough, and securing the portion of the flexible member to the fixation member may include passing the portion of the flexible member through the hole of the fixation member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 3A is a perspective view of a flexible member of the spinal fixation construct of FIG. 1;

FIG. 3B is a cross-sectional view of the flexible member of FIG. 3A, taken along lines 3B-3B of FIG. 3A;

FIGS. 4A and 4B are cross-sectional views of flexible members in accordance with other embodiments of the present disclosure;

FIGS. 4C and 4D are side views of flexible members in accordance with yet other embodiments of the present disclosure;

FIGS. 5A-5D are cross-sectional views of flexible members in accordance with embodiments of the present disclosure;

DETAILED DESCRIPTION

Figure 1:
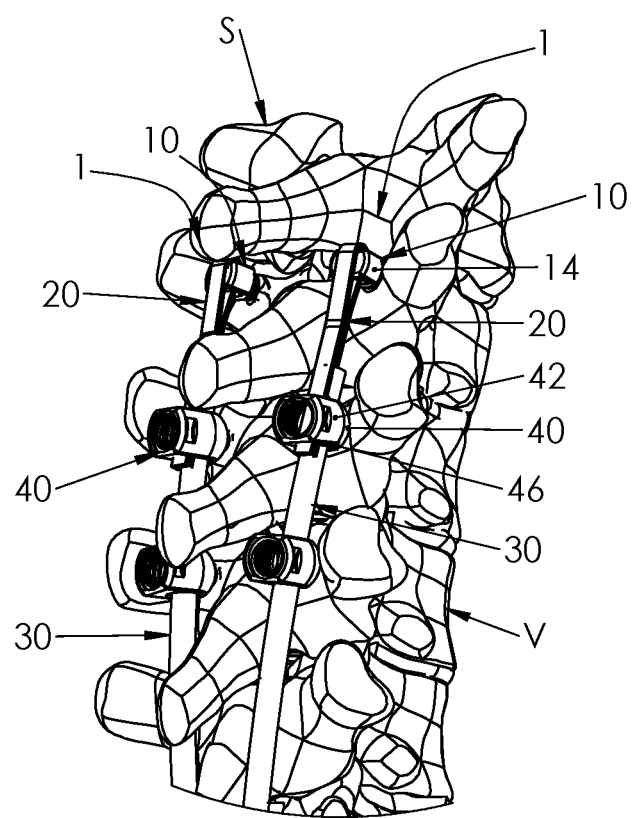
FIG. 1 is an in situ view of a spinal fixation construct in accordance with an embodiment of the present disclosure.

Embodiments of the present disclosure are now described in detail with reference to the drawings in which like reference numerals designate identical or corresponding elements in each of the several views. The term "clinician" refers to a doctor (e.g., a surgeon), a nurse, or any other care provider, and may include support personnel. Throughout this description, the term "proximal" refers to a portion of a device or component thereof that is closer to a clinician, and the term "distal" refers to the portion of the device or component thereof that is farther from the clinician. "Cranial" refers to a spine segment closer to the head of a patient, whereas "caudal" refers to the spine segment closer to the feet of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring initially to FIG. 1, a spinal fixation construct 1 in accordance with an embodiment of the present disclosure includes a fixation member 10, a flexible member 20, a spinal rod 30, and at least one bone screw 40. While two spinal fixation constructs 1 are shown in FIG. 1, the spinal fixation constructs 1 are discussed singularly as they are substantially identical.

Figure 2:
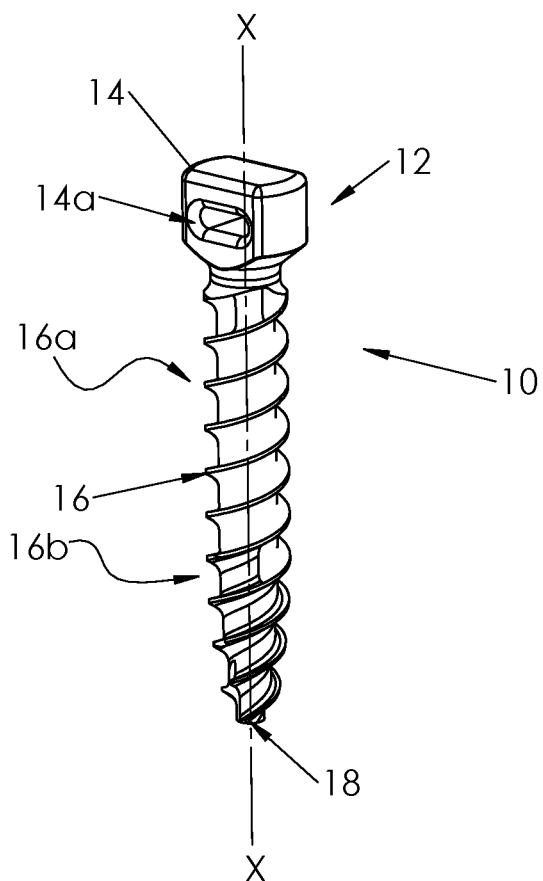
FIG. 2 is a perspective view of a fixation member of the spinal fixation construct of FIG. 1.

As shown in FIG. 2, the fixation member 10 includes a proximal end 12 including a head portion 14, and a threaded body portion 16 extending distally from the head portion 14 to a distal tip 18 along a longitudinal axis "X". The head portion 14 of the fixation member 10 defines a hole 14a therethrough that is configured and dimensioned to receive and retain a portion of the flexible member 20 (see e.g., FIG. 1). The hole 14a has a lateral dimension that is larger than a longitudinal dimension of the hole 14a. The threaded body portion 16 of the fixation member 10 includes a first threaded region 16a and a second threaded region 16b. The fixation member 10 is formed or machined from a biocompatible metallic material including, but not limited to, titanium alloy, stainless steel, and cobalt chrome.

As shown in FIG. 3A, the flexible member 20 includes an elongated body 22 having a first end portion 22a and a second end portion 22b. The flexible member 20 is formed from a biocompatible material having a lower modulus of elasticity than the biocompatible material of the fixation member 10 (see e.g., FIG. 2) and thus, the flexible member 20 is formed of a less stiff material than that of the fixation member 10. The flexible member 20 may be fabricated from one or more polymeric materials such as, but not limited to, polyethylene, ultra-high molecular weight polyethylene, polypropylene, polyetherimide, polysulfone, polyacetal, nylon, polytetrafluoroethylene, and combinations thereof, and may be formed by injection molding, extruding, compression molding, overmolding, machining or other known methods for shaping polymeric materials as within the purview of those skilled in the art.

The elongated body 22 of the flexible member 20 has a uniform dimension along the length thereof, and as shown in FIG. 3B, is a solid monolithic structure having a generally rectangular cross-sectional shape. It is envisioned that the dimensions of the elongated body 22 of the flexible member 20 may vary along the length thereof.

Other configurations of the flexible member 20 are also contemplated. For example, in some embodiments, as shown in FIG. 4A, the elongated body 22a of a flexible member 20a may have an opening 23 defined therethrough to increase the flexibility of the flexible member 20a. In some embodiments, the flexible member may be a composite. As shown, for example, in FIG. 4B, an elongated body 22b of a flexible member 20b has a core 25a and sheath 25b configuration in which the core 25a and sheath 25b may be formed of the same or different materials having the same or different moduli of elasticities. As shown in FIG. 4C, an elongated body 22c of a flexible member 20c has a braided configuration in which first strand(s) 27a of the elongated body 22c are formed from the same or different material having the same or different modulus of elasticity than second strand(s) 27b of the elongated body 22c. As another example, as shown in FIG. 4D, an elongated body 22d of a flexible member 20d has a layered configuration including two or more layers 29a, 29b which may be formed from the same or different materials having the same or different modulus of elasticities. Additionally or alternatively, in non-limiting examples, the flexible member may have other cross-sectional shapes, such as a flexible member 20e having a circular shape (FIG. 5A), a flexible member 20f having an elliptical shape (FIG. 5B), a flexible member 20g having a triangular shape (FIG. 5C), a flexible member 20h having a semi-circular shape (FIG. 5D), etc.

It should be understood that the combination of, for example, size, configuration, shape, and/or material selection of the elongated body of the flexible member provides the flexible member with a desired stiffness profile along the length thereof for a desired surgical application.

Figure 6:
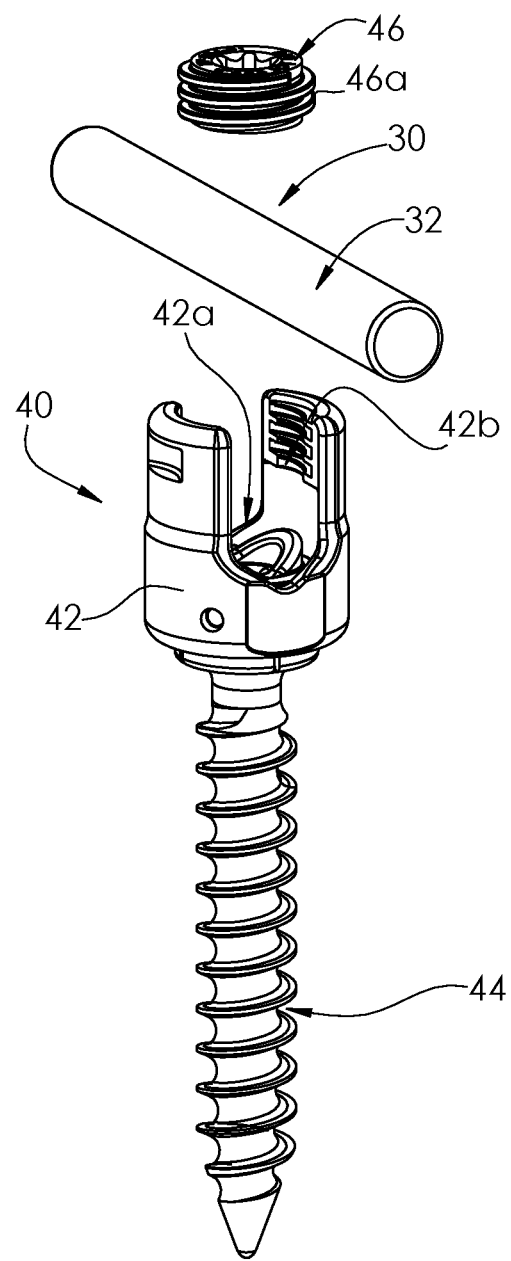
FIG. 6 is a perspective view of a spinal rod and a bone screw of the spinal fixation construct of FIG. 1.

As shown in FIG. 6, the spinal rod 30 includes an elongated body 32 having opposed ends, and the bone screw 40 includes a housing 42, a bone screw member 44, and a set screw 46. Housing 42 of bone screw 40 includes a saddle portion 42a within which the spinal rod 30 may be seated. Housing 42 also includes internal threads 42b configured to engage complementary external threads 46a of the set screw 46 to secure the set screw 46 within the housing 42 and to secure the spinal rod 30 within the saddle portion 42a of the housing 42. Suitable spinal rods and bone screws for use in the spinal fixation construct of the present disclosure are shown and described in U.S. Patent Application Publication Nos. 2013/0013003 and 2013/0144342, and U.S. Pat. No. 8,882,817, the disclosures of which are herein incorporated by reference in their entireties. The spinal rod 30 and bone screw(s) 40 are formed from biocompatible metallic materials, such as those listed above with regard to the fixation member 10 and thus, the flexible member 20 is formed of a less stiff material than that of the spinal rod 30 and the bone screw(s) 40.

Referring again to FIG. 1, in an embodiment of use, the fixation member 10 is implanted within a bony element of a spine "S," such as the pedicle or facet. The bone screws 40 are implanted into vertebral bodies "V" of the spine "S" in spaced relation relative to the fixation member 10 and relative to each other, and the spinal rod 30 is positioned within the bone screws 40. The flexible member 20 is passed through the hole 14a (see e.g., FIG. 2) of the head portion 14 of the fixation member 10 such that a portion of the flexible member 20 is secured within the head portion 14 of the fixation member 10, and the first and second end portions 22a and 22b (see e.g., FIG. 3A) of the flexible member 20 are placed adjacent to the spinal rod 30 within the saddle portion 42a (see e.g., FIG. 6) of the housing 42 of the bone screw 40, and secured therein by the set screw 46 which compresses the flexible member 20 against the spinal rod 30.

Figure 7:
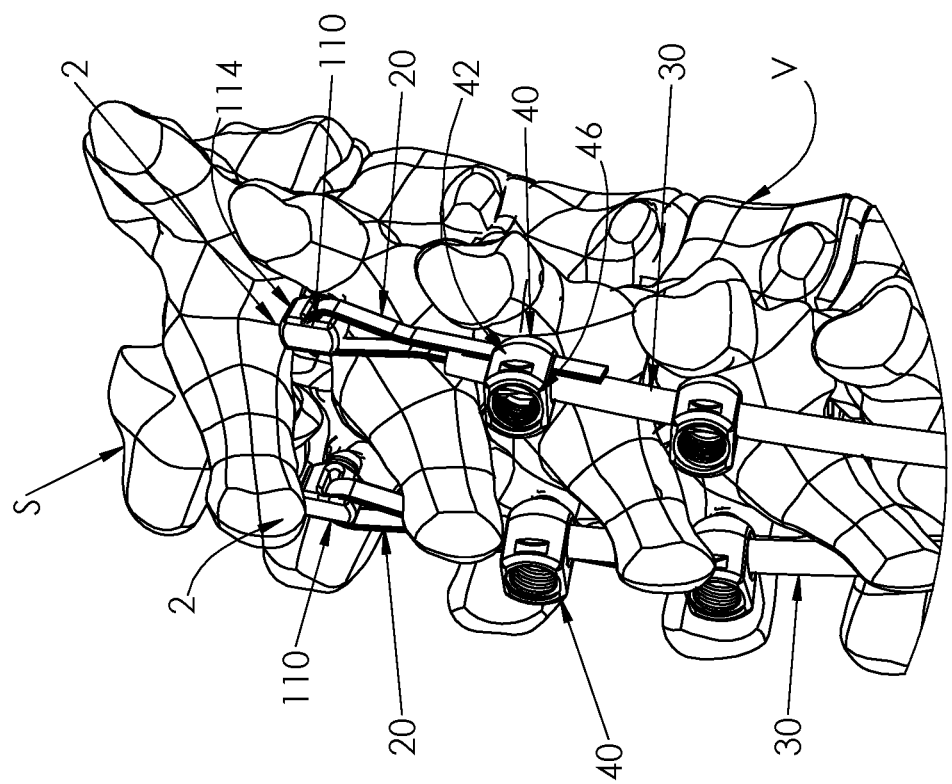
FIG. 7 is an in situ view of a spinal fixation construct in accordance with another embodiment of the present disclosure.
Figure 8:
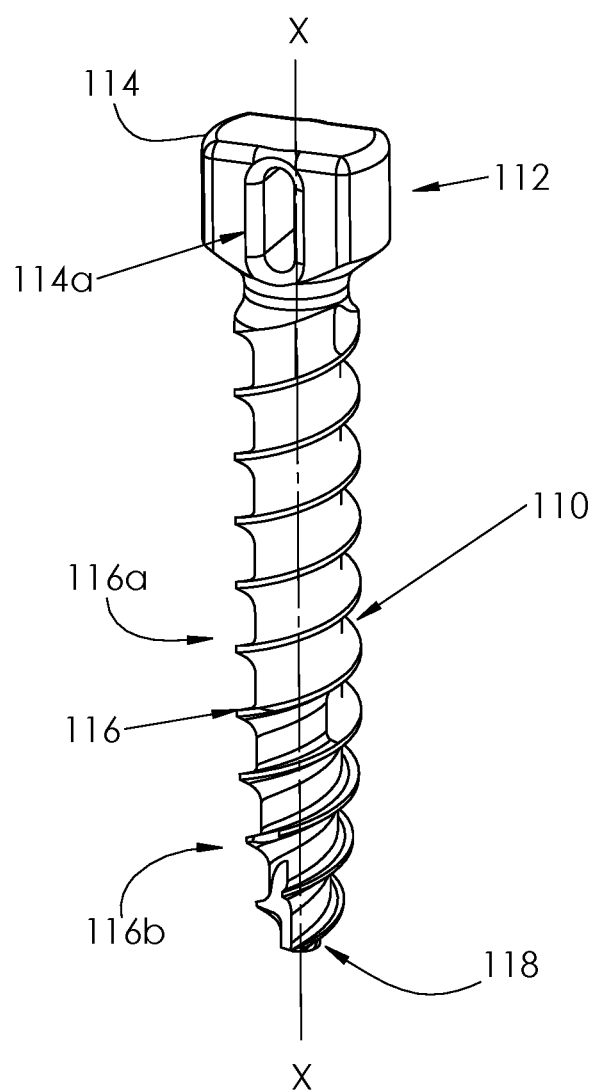
FIG. 8 is a perspective view of a fixation member of the spinal fixation construct of FIG. 7.

Referring now to FIG. 7, a spinal fixation construct 2 in accordance with another embodiment of the present disclosure includes a fixation member 110, a flexible member 20, a spinal rod 30, and at least one bone screw 40. As shown in FIG. 8, the fixation member 110 includes a proximal end 112 including a head portion 114 and a threaded body portion 116 extending distally from the head portion 114 to a distal tip 118 along a longitudinal axis "X". The head portion 114 of the fixation member 110 defines a hole 114a therethrough that is configured and dimensioned to receive a portion of the flexible member 20 (see e.g., FIG. 7). The hole 114a has a lateral dimension that is smaller than a longitudinal dimension of the hole 114a. The threaded body portion 116 of the fixation member 110 includes a first threaded region 116a and a second threaded region 116b.

In an embodiment of use, as shown in FIG. 7, the fixation member 110 is implanted within a bony structure of a spine "S," such as the pedicle or facet. The bone screws 40 are implanted into vertebral bodies "V" of the spine "S" in spaced relation relative to the fixation member 110 and relative to each other, and the spinal rod 30 is positioned within the bone screws 40. The flexible member 20 is passed through the hole 114a (see e.g., FIG. 8) of the head portion 114 of the fixation member 110 such that a portion of the flexible member 20 is secured within the head portion 114 of the fixation member 110, and the first and second end portions 22a and 22b (see e.g., FIG. 3A) of the flexible member 20 are placed adjacent to the spinal rod 30 within the saddle portion 42a (see e.g., FIG. 6) of the housing 42 of the bone screw 40, and secured therein by the set screw 46.

Figure 9:
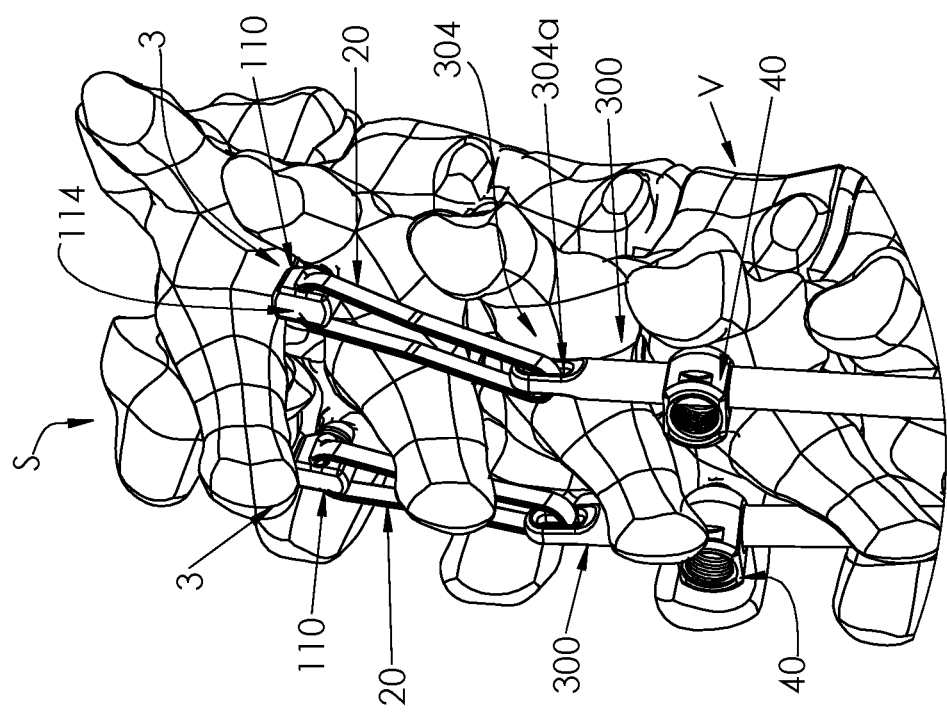
FIG. 9 is an in situ view of a spinal fixation construct in accordance with yet another embodiment of the present disclosure.
Figure 10B:
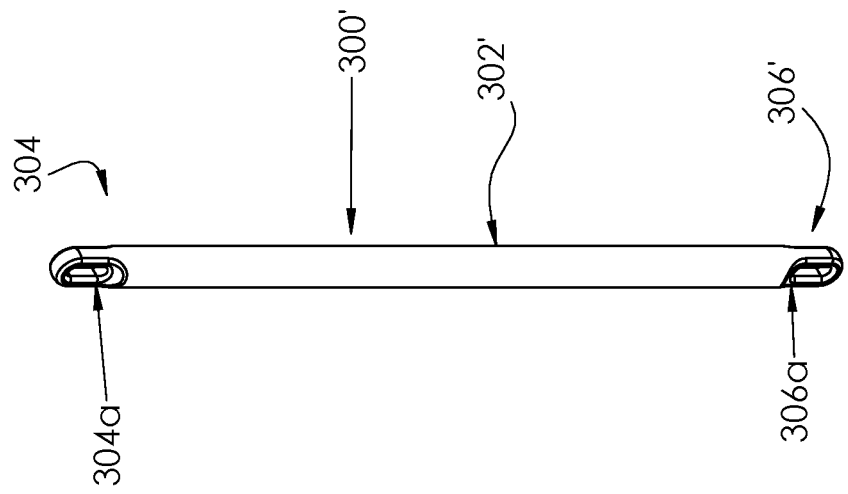
FIG. 10B is a perspective view of a spinal rod in accordance with another embodiment of the present disclosure.
Figure 10A:
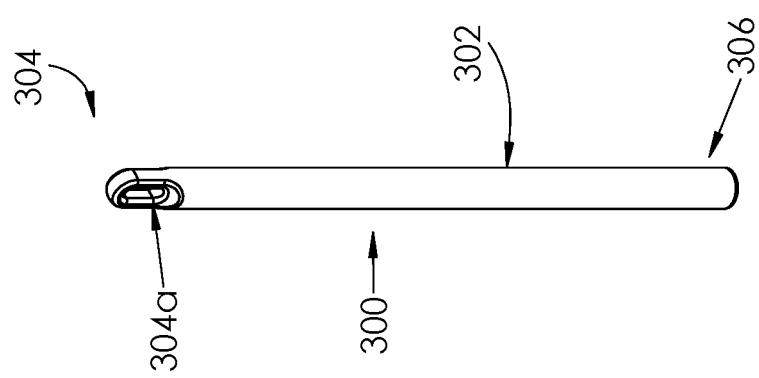
FIG. 10A is a perspective view of a spinal rod of the spinal fixation construct of FIG. 9.

Referring now to FIG. 9, a spinal fixation construct 3 in accordance with another embodiment of the present disclosure includes a fixation member 110, flexible member 20, a spinal rod 300, and at least one bone screw 40. As shown in FIG. 10A, the spinal rod 300 includes an elongated body 302 having a first end 304 and a second end 306. The first end 304 defines an aperture or through hole 304a therethrough which is configured and dimensioned to engage a portion of the flexible member 20 (see e.g., FIG. 9). In some embodiments, shown in FIG. 10B, a spinal rod 300' includes an elongated body 302' having a first end 304 defining an aperture 304a therethrough, and a second end 306' defining an aperture 306a therethrough for use with a flexible member.

In an embodiment of use, shown in FIG. 9, the fixation member 110 is implanted within a bony element of a spine "S," the bone screw 40 is implanted into a vertebral body "V" of the spine "S" in spaced relation relative to the fixation member 110, and the spinal rod 300 is positioned within the bone screw 40. The flexible member 20 is passed through the hole 114a (see e.g., FIG. 8) of the fixation member 110 and the aperture 304a of the spinal rod 300 such that portions of the flexible member 20 are secured within the head portion 114 of the fixation member 110 and the first end 304 of the spinal rod 300. The first and second end portions 22a and 22b (see e.g., FIG. 3A) of the flexible member 20 are secured, e.g., by being tied or clamped, to the fixation member 110, the spinal rod 300, and/or to each other, such that the flexible member 20 forms a continuous loop.

Figure 11:
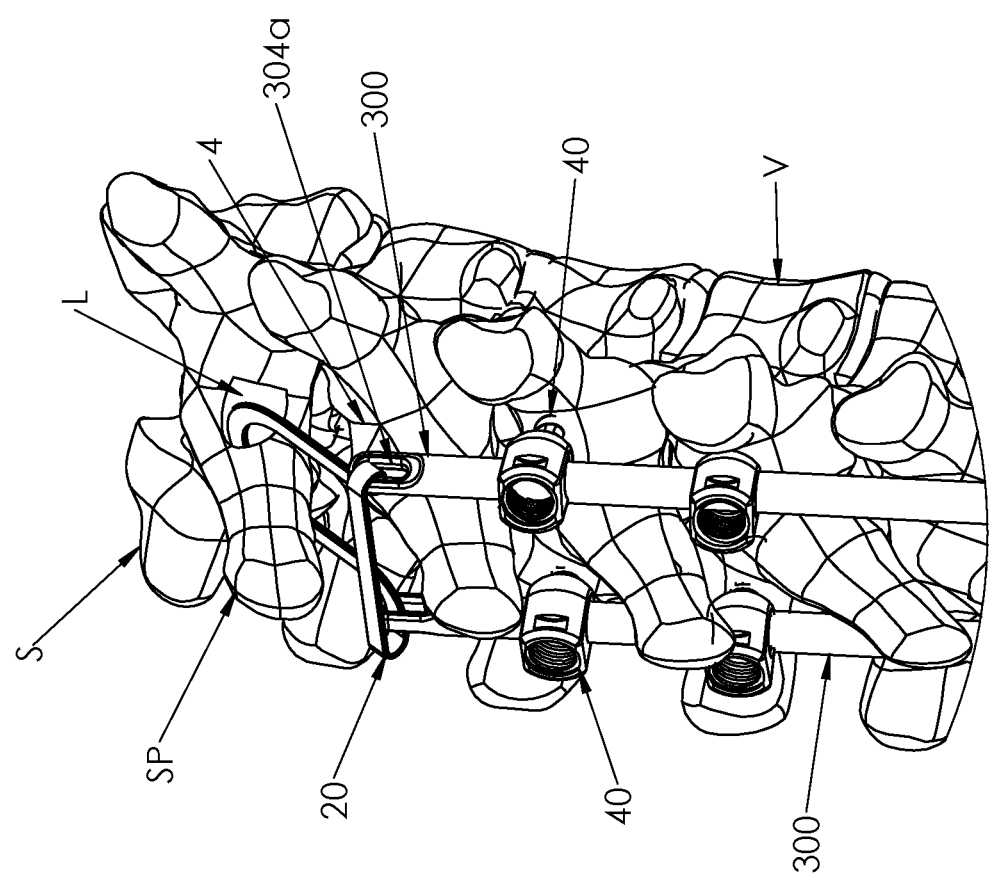
FIG. 11 is an in situ view of a spinal fixation construct in accordance with yet another embodiment of the present disclosure.

Referring now to FIG. 11, a spinal fixation construct 4 in accordance with another embodiment of the present disclosure includes a flexible member 20, two spinal rods 300, and a plurality of bone screws 40. In an embodiment of use, the bone screws 40 are implanted into vertebral bodies "V" of the spine "S," on opposed sides of the spinous process "SP," and the spinal rods 300 are positioned within the bone screws 40. The flexible member 20 is passed through the apertures 304a of the spinal rods 300 such that portions of the flexible member 20 are retained therein, and the flexible member 20 is looped around a lamina "L" of the spine "S." The first and second end portions 22a, 22b (FIG. 3A) of the flexible member 20 are secured, e.g., by being tied or clamped, to the spinal rod(s) 300 and/or to each other.

Figure 12:
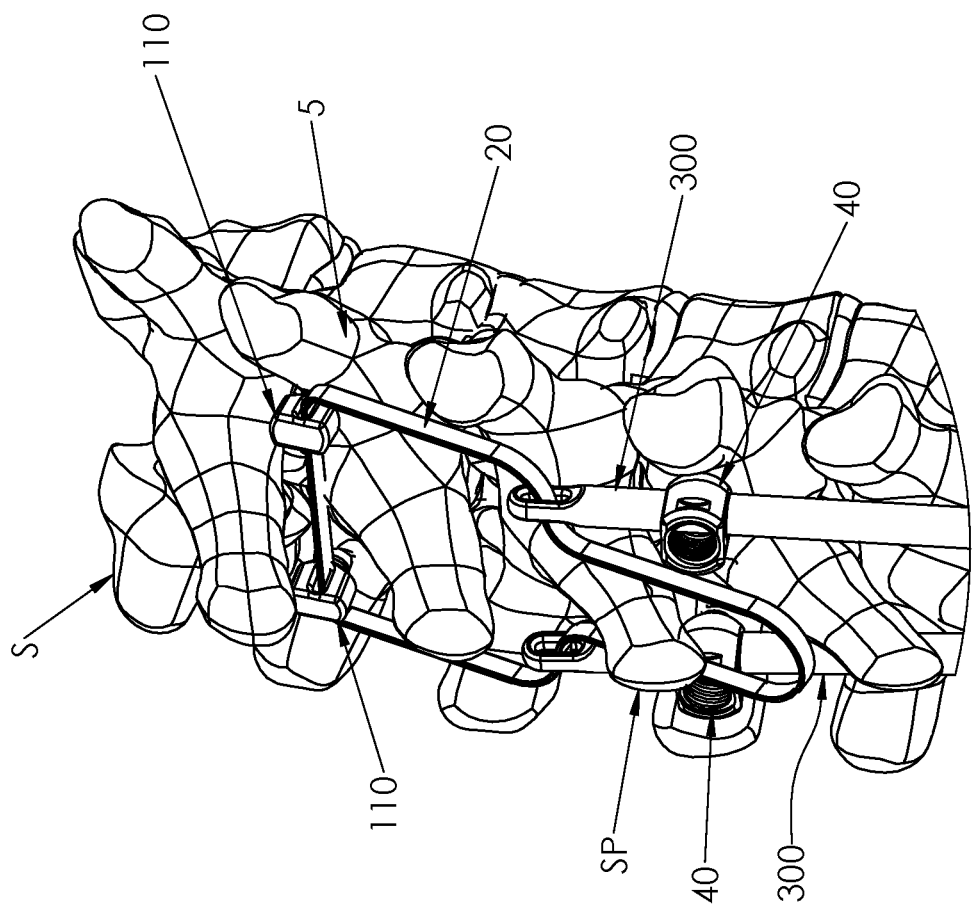
FIG. 12 is an in situ view of a spinal fixation construct in accordance with another embodiment of the present disclosure.

As shown in FIG. 12, a spinal fixation construct 5 in accordance with another embodiment of the present disclosure includes two fixation members 110, a flexible member 20, two spinal rods 300, and a plurality of bone screws 40. In an embodiment of use, the fixation members 110 are implanted within a bony element of a spine "S" on opposed sides of the spinous process "SP." The bone screws 40 are implanted into vertebral bodies "V" of the spine "S" in spaced relation relative to the fixation members 110, also on opposed sides of the spinous process "SP," and the spinal rods 300 are positioned within the bone screws 40. The flexible member 20 is passed through the holes 114a (see e.g., FIG. 8) of the fixation member 110 and the apertures 304a of the spinal rods 300, such that the flexible member 20 is looped around the spinous process "SP." The first and second end portions 22a, 22b (FIG. 3A) of the flexible member 20 are secured, e.g., by being tied or clamped, to the fixation member 110, the spinal rod 300, and/or to each other.

While the embodiments of the spinal fixation constructs 1-5 have been shown with the flexible member 20 oriented in a cranial orientation to facilitate reducing the stress impact on the cranial, non-instrumented adjacent level to the spinal fixation construct 1-5, it should be understood that if a less stiff portion is desired at the caudal end of the spinal fixation construct 1-5, the spinal fixation construct 1-5 may be turned 180 degrees to allow the flexible member 20 to be located in a caudal orientation and/or the spinal fixation construct 1-5 may be stopped one level above the desired level. Should both the cranial and caudal ends require less stiffness, both ends may include the flexible member 20. Further, as discussed above, the modulus of elasticity of the flexible member 20 is different from the modulus of elasticity of the other components of the spinal fixation construct 1-5 (e.g., the spinal rod 30, 300, 300'), and thus, a range of motion is maintained between adjacent vertebrae without spinal fusion.

Figure 13:
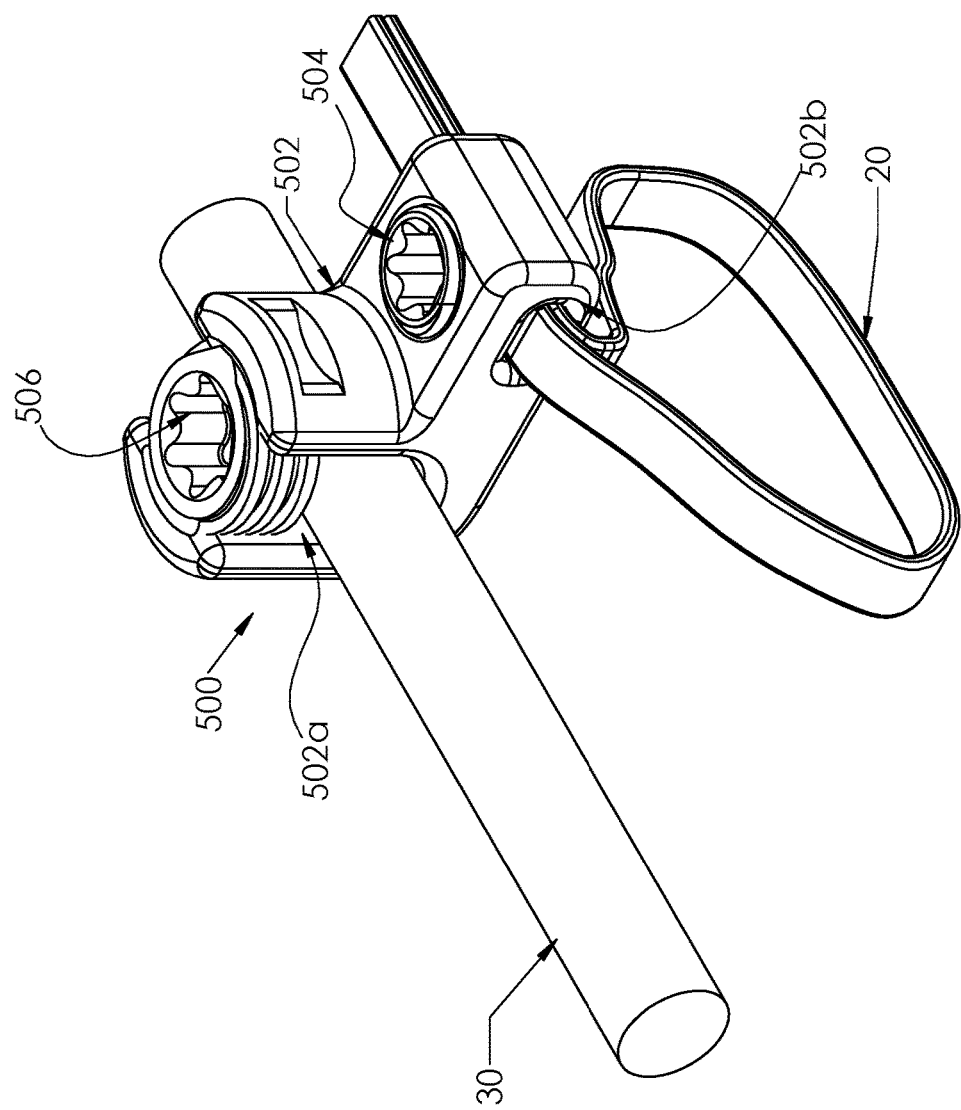
FIG. 13 is a perspective view of a spinal implant for use with a spinal fixation construct of the present disclosure.

Other embodiments are also envisioned. For example, the flexible member may be configured to loop around a portion of a bony element, such as a vertebral body, and coupled to a spinal rod with a spinal implant, such as an implant depicted in U.S. Patent Application No. 2014/0257397, the disclosure of which is herein incorporated by reference in its entirety. As shown in FIG. 13, the spinal implant 500 includes an implant housing 502 that defines a rod passage 502a and an implant passage 502b. The rod passage 502a is configured to receive a portion of a spinal rod 30 and the implant passage 502b is configured to receive a portion of the flexible member 20. An implant set screw 504 engages the flexible member 20 when the flexible member 20 is received within the implant passage 502b to fix the flexible member 20 relative to the implant housing 502, and a rod set screw 506 engages the spinal rod 30 disposed within the rod passage 502a to fix the spinal rod 30 relative to the implant housing 502. Further, a surgical instrument, such as that described in commonly owned U.S. patent application Ser. No. 14/644,428, the disclosure of which is herein incorporated by reference in its entirety, may be used by a clinician to tension the flexible member 20 about the bony element and/or fix the flexible member 20 to the spinal implant 500.

The spinal fixation construct may be provided in a kit. The kit is an assembled package with at least one flexible member, at least one fixation member, at least one spinal rod, and/or bone screw(s). The kit may include any and/or all of the configurations of: the flexible member 20, 20a-20h; the fixation members 10, 110; the spinal rods 30, 300, 300'; and/or the bone screws 40, described above. The kit may include a plurality of flexible members, fixation members, spinal rods, and/or bone screws having, for example, different configurations, diameters, lengths, and/or shapes. Accordingly, a clinician may pick and choose components to form a spinal fixation construct with a desired stiffness profile for a surgical procedure.

In embodiments, a clinician may perform any required anterior procedures and then turn the patient to a prone position. In the prone position, the clinician can create a spinal fixation construct which may be a combination of any of the components described above, and include additional components, such as bone anchors, transverse connectors, etc. The clinician implants any fixation members, bone screws, and/or bone anchors, and spinal rods posteriorly, and then supplements the posterior instrumentation with the flexible member. The flexible member may be looped over the lamina, through the spinous process, over the spinous process, or anchored to a fixation member and/or a spinal rod, as desired by the clinician for the particular surgical procedure. The first and second end portions of the flexible member may be placed in the saddle portion of a bone screw adjacent the spinal rod and locked in place by the set screw of the bone screw, one or both end portions may be tied through a through hole of a fixation member and/or a spinal rod, as desired by the clinician for the particular surgical procedure. The flexible member may be placed at the cranial and/or caudal end of the spinal fixation construct.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A spinal fixation construct comprising:
   a spinal implant defining a rod passage;
   a first spinal rod including a body and an aperture defined along the body, formed directly through the body, and enclosed by the body, a portion of the spinal rod positioned within the rod passage;
   a first monolithic fixation member including a threaded shaft and a head portion defining a passageway; and
   a first flexible member defining a loop, a portion of the loop extending entirely through the aperture of the spinal rod, wherein the first flexible member extends from the aperture of the spinal rod and through the passageway of the head portion of the first fixation member.

2. The spinal fixation construct of claim 1, wherein the aperture of the first spinal rod is defined at a first end of the spinal rod.

3. The spinal fixation construct of claim 1, wherein the first spinal rod includes a second aperture defined along the body.

4. The spinal fixation construct of claim 3, wherein the aperture of the first spinal rod is defined at a first end of the first spinal rod and the second aperture of the first spinal rod is defined at a second end of the first spinal rod.

5. The spinal fixation construct of claim 1, further comprising a first fixation member including a head portion defining a passageway.

6. The spinal fixation construct of claim 5, wherein the first flexible member extends from the aperture of the spinal rod and through the passageway of the head portion of the first fixation member.

7. The spinal fixation construct of claim 6, further comprising:
   a second fixation member including a head portion defining a passageway therethrough; and
   a second spinal rod including a body and an aperture defined along the body of the second spinal rod.

8. The spinal fixation construct of claim 7, further comprising a second flexible member extending through the aperture of the second spinal rod and through the passageway of the head portion of the second fixation member.

9. The spinal fixation construct of claim 8, wherein the first rod and the first flexible member extends parallel to the second rod and the second flexible member.

10. The spinal fixation construct of claim 7, wherein the first flexible member extends through the aperture of the second spinal rod and through the hole of the head portion of the second fixation member.

11. The spinal fixation construct of claim 10, wherein the first flexible member is configured to be looped about a bony element.

12. The spinal fixation construct of claim 5, wherein the first flexible member is wrapped about a portion of the head portion of the first fixation member.

13. The spinal fixation construct of claim 12, wherein the first flexible member is wrapped about an axis parallel to a central axis defined by the fixation member.

14. A spinal fixation construct comprising:
    a spinal implant defining a rod passage;
    a first spinal rod including a body extending between a first end and a second end along a longitudinal axis and an aperture formed directly through the body and enclosed by the body, a portion of the spinal rod positioned within the rod passage;
    a first monolithic fixation member including a threaded shaft and a head portion defining a passageway; and
    a first flexible member defining a loop connected to the aperture of the first spinal rod, such that a portion of the flexible member defining the loop is substantially parallel to the longitudinal axis of the rod and extends beyond the first end of the spinal rod, wherein the first flexible member extends from the aperture of the spinal rod and through the passageway of the head portion of the first fixation member.

15. The spinal fixation construct of claim 14, wherein the first spinal rod includes the aperture defined along the body at the first end of the spinal rod.

16. The spinal fixation construct of claim 15, wherein the first spinal rod includes a second aperture defined along the body at the second end of the spinal rod.

17. The spinal fixation construct of claim 14, further comprising a first fixation member including a head portion defining a passageway.

18. The spinal fixation construct of claim 17, wherein the first flexible member extends through the passageway of the head portion of the first fixation member.

19. The spinal fixation construct of claim 17, wherein the first flexible member extends from the aperture of the spinal rod and through the passageway of the head portion of the first fixation member.

20. The spinal fixation construct of claim 17, wherein the first flexible member is wrapped about a portion of the head portion.

* * * * *